Sept. 18, 1962 R. V. LINDQUIST Plant Pat. 2,173
ROSE PLANT
Filed Oct. 31, 1961
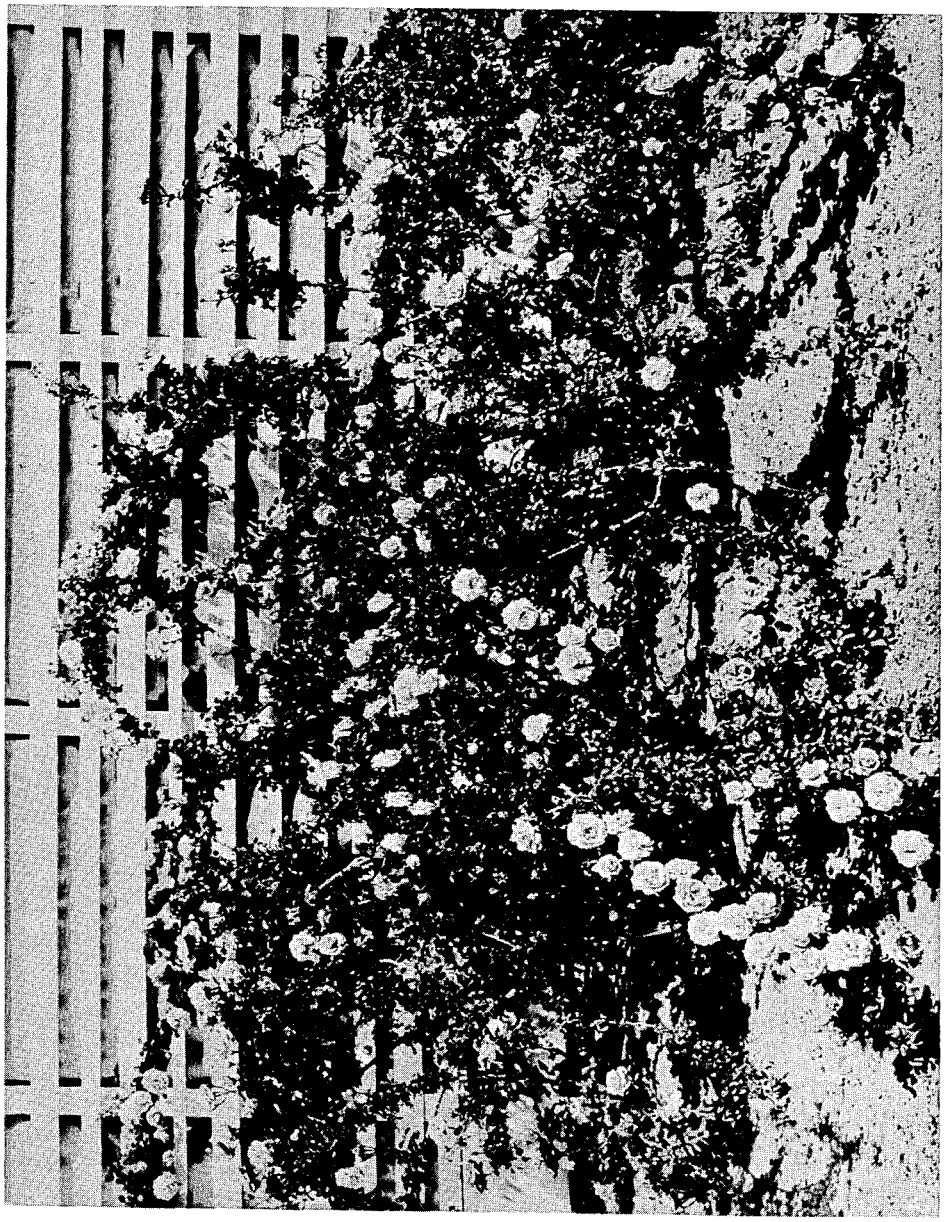
INVENTOR
Robert V. Lindquist
BY Robb & Robb
ATTORNEYS United States Patent Office Plant Pat. 2,173
Patented Sept. 18, 1962

2,173
ROSE PLANT

Robert V. Lindquist, Hemet, Calif., assignor to Hemet Wholesale, Hemet, Calif., a partnership Filed Oct. 31, 1961, Ser. No. 149,137
1 Claim. (Cl. 47—61)

The present invention relates to a new and distinct variety of rose plant of the climber class, which originated as a sport of the variety "Tom Tom" (Plant Patent No. 1,671) from which it is distinguished primarily by its climbing habit of growth.

The new sport was discovered by me in the cultivated fields of my assignee, located near Hemet, California, where the parent variety "Tom Tom" was being grown commercially. At the time of my discovery, my attention was attracted to the new variety by the usually vigorous and climbing habit of a particular plant amongst the field plants of the variety "Tom Tom." Upon closer examination thereof, I found that the parent variety had sported, and I thereupon promptly took steps to preserve the sport, keep it under observation, and later on to asexually reproduce the same. As the result of these observations of the original sport and the progeny thereof as asexually reproduced by me by budding in the nursery fields of my assignee aforesaid, I have fully confirmed that the climbing habit of the new variety is definitely fixed and established, and is transmissible by asexual reproduction.

So far as I am aware, the parent variety "Tom Tom" has never before exhibited any tendency toward a climbing habit of growth, but has heretofore conformed to the usual habit of a bush rose of the hybrid polyantha class. Accordingly, the climbing habit of the new sport represents a unique and highly desirable characteristic in combination with the other characteristics of the new rose which are generally similar to those of the parent variety. In view of these general similarities, except for the climbing habit of growth, it is unnecessary to describe or illustrate the new variety in detail herein, but for convenience, the accompanying drawing illustrates in black-and-white typical specimen plants of the new variety to show their climbing habit of growth, as well as typical specimens of the flower and foliage in different stages of development and as borne by the clambing plants.

Also, for convenience, the following description of my new variety is given, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Climber; outdoor; sport; for cut flowers and for garden decoration.
Class: Climbing hybrid polyantha.
Parentage: Sport of "Tom Tom."
Propagation: Holds its distinguishing characteristics through succeeding propagations by budding.

*Flower*

Locality where grown and observed: Hemet, California.
Flowers borne: Usually from 3 to 5 to stem; in irregular flat cluster; on strong stems of medium length.
Quantity of bloom: Very free, outdoors.
Continuity: Heavy spring bloom, with continuous lighter bloom through growing season.
Fragrance: Slight. Nature—spicy.
Bud:
*Peduncle.*—Average length; average caliper; erect; moderately smooth; few gland-tipped cilia; few prickles. Color—near Biscay Green, Plate XVII (Ridgway).

*Before calyx breaks.*—Size—medium. Form—medium length; pointed; with foliaceous appendages; with few gland-tipped cilia and glandular bloom on the surface of the bud; usually with slender bristle-like parts extending beyond the tip of the bud equal to ¼ or more of its length.
*As calyx breaks.*—Color—near China Rose, Plate 024, page 111 (Wilson).
*Sepals.*—Inner surface—with fine wooly tomentum. Margins—with gland-tipped cilia.
*As first petal opens.*—Size—average. Form—medium length; ovoid. Color: outside—near China Rose, Plate 024/1, page 111 (Wilson), with base near Primrose Yellow, Plate 601/3, page 65 (Wilson); inside—near Neyron Rose, Plate 623/1, page 76 (Wilson), with base near Primrose Yellow, Plate 601/3, page 65 (Wilson).
*Opening.*—Opens up well; is not retarded from opening by cold, hot, wet or dry weather.
Bloom:
*Size (when fully open).*—Average; from 3 inches to 3½ inches.
*Petalage.*—Double; from 23 to 27 petals, plus 5 to 8 petaloids; arranged irregularly.
*Form.*—From flat to high-centered at first, but becoming flat to open; petals being at first somewhat cupped, with tips rolled outward, but later becoming somewhat flat, with tips rolled outward at maturity.
Petals:
*Texture.*—Meduim thickness. Inside—satiny. Outside—from slightly shiny to satiny.
*Shape.*—Outside—round, with apex flat. Intermediate—oval, with apex flat. Inside—nearly oval, with apex flat.

This description of a newly opened flower was made from a rose grown outdoors during the month of April at Hemet, California:

Color.—Outer petal: outside surface—near Tyrian Rose, Plate 24/2, page 24 (Wilson), with base near Primrose Yellow, Plate 601/3, plate 65 (Wilson); inside surface—near Neyron Rose, Page 623/1, page 76 (Wilson), with base near Primrose Yellow, Plate 601/3, page 65 (Wilson). Intermediate petal: outside surface—near Tyrian Rose, Plate 24/2, page 24 (Wilson), with base near Primrose Yellow, Plate 601/3, page 65 (Wilson); inside surface—near Neyron Rose, Plate 623/1, page 76 (Wilson), with base near Primrose Yellow, Plate 601/3, page 65 (Wilson). Inner petal: outside surface—near Tyrian Rose, Plate 24/2, page 24 (Wilson), with base near Primrose Yellow, Plate 601/3, page 65 (Wilson); inside surface—near Neyron Rose, Plate 623/1, page 76 (Wilson), with base near Primrose Yellow, Plate 601/3, page 65 (Wilson).

This description was made from a rose that was open for 3 days outdoors during the month of April at Hemet, California:

*Color.*—Outer petal: outside surface—near Tyrian Rose, Plate 24/2, page 24 (Wilson), with base near Primrose Yellow, Plate 601/3, page 65 (Wilson); inside surface—near Rose Bengal, Plate 25/2, page 25 (Wilson), with base near Primrose Yellow, Plate 601/3, page 65 (Wilson). Inner petal: outside surface—near Tyrian Rose, Plate 24/2, page 24 (Wilson), with base near Primrose Yellow, Plate 601/3, page 65 (Wilson); inside surface—near Rose Bengal, Plate 25/1, page 25 (Wilson), with base near Primrose Yellow, Plate 601/3, page 65 (Wilson).

*General color effect.*—Newly opened flower—near Neyron Rose, Plate 623/1, page 76 (Wilson). 3-days open—near Neyron Rose, Plate 623/1, page 76 (Wilson).

*Behavior.*—Drop off cleanly, except some which persist under certain weather conditions.

*Flower longevity.*—On bush in garden—from 2 to 4 days in April. Cut roses grown outdoors and kept at living-room temperatures—2 or 3 days in April.

*Reproductive Organs*

Stamens: Average number; arranged regularly about pistils.

Filaments: Medium length; most with anthers. Color—near China Rose, Plate 024/1, page 111 (Wilson) at base, shading to near China Rose, Plate 024/3, page 111 (Wilson).

Anthers: Medium size; all open at approximately same time. Color: upper side—near Ochraceous Buff, Plate XV (Ridgway); under side—near Ochraceous Buff, Plate XV (Ridgway).

Pollen: Somewhat moderate. Color—near Straw Yellow, Plate 604, page 67 (Wilson).

Pistils: Average number (approximately 75).

Styles: Moderately even; average length; thin; somewhat bunched.

Stigma: Color—near Orange Buff, Plate 507/2, page 133 (Wilson).

Ovaries: Usually most enclosed in, but some protruding from, calyx.

Hips: Average length; pear-shaped; moderately smooth; walls fleshy. Color—near Spanish Orange, Plate 0/0, page 103 (Wilson).

Sepals: Falling soon; moderately long. Color: inside—near Pale Fluorite Green, Plate XXXII (Ridgway); outside—near Light Bice Green, Plate XVII (Ridgway).

Seeds: Few (from 8 to 20 in number); usually from small to medium size.

*Plant*

Foliage:

*Leaves.*—Compound of usually 3 to 5 leaflets; abundant; medium size; moderately heavy; semi-glossy.

*Leaflets.*—Shape—oval, with apex mucronate. Base—obtuse. Margin—irregularly serrate.

*Color.*—Mature: upper surface—near Dark Yellowish Green, Plate XVIII (Ridgway), with some shadings of near Nickle Green, Plate XXXIII (Ridgeway); under surface—near Chromium Green, Plate XXXII (Ridgway). Young: upper surface—near Cedar Green, Plate VI (Ridgway) at center of leaf, shading to near Dark Corinthian Purple, Plate XXXVIII (Ridgway); under surface—near Dark Corinthian Purple, Plate XXXVIII (Ridgway).

Rachis (the supporting stem of the compound leaf.—Average size. Upper side—grooved; with some stipitate glands on edges; some prickles. Under side—moderately prickly; with few stipitate glands.

*Stipules.*—Medium length; medium width; with points of medium length turning out at an angle of about 45°.

*Disease resistance.*—Mildly subject to mildew, as determined from comparison with other varieties grown under comparable cultural conditions at Hemet, California.

Growth:

*Habit.*—Climbing; much-branched.

*Growth.*—Vigorous.

*Canes.*—From medium caliper to heavy.

*Main stems.*—Color—near Oil Green, Plate V (Ridgway). Large prickles—several; from medium length to long; hooked slightly downward; with moderately narrow base of medium length; color—near Russet, Plate XV (Ridgway). Small prickles—none. Hairs—none.

*Branches.*—Color—near Spinach Green, Plate V (Ridgway), with occasional shadings of Corinthian Purple, Plate XXXVIII (Ridgway). Large prickles—from several to many; medium length; hooked slightly downward; with moderately narrow base of medium length; color—near Russet, Plate XV (Ridgway). Small prickles—none. Hairs—none.

*New shoots.*—Color—near Dark Corinthian Purple, Plate XXXVIII (Ridgway), with occasional areas of near Chromium Green, Plate XXXII (Ridgway). Large prickles—several; medium length; hooked slightly downward; with moderately narrow base of medium length; color—near Corinthian Purple, Plate XXXVIII (Ridgway). Small prickles—few. Hairs—none.

I claim:

A new and distinct variety of rose plant of the climbing hybrid polyantha class, substantially as herein shown and described, characterized particularly as to novelty by being generally similar to its parent variety "Tom Tom" (Plant Patent No. 1,671), but being essentially distinguished therefrom by its climbing habit of growth.

No references cited.